(12) United States Patent
Daynes et al.

(10) Patent No.: US 10,107,801 B2
(45) Date of Patent: Oct. 23, 2018

(54) FLOW ASSAY METHOD FOR AN OBJECT OF INTEREST

(71) Applicants: HORIBA ABX SAS, Montpellier (FR); Jerome Bibette, Paris (FR)

(72) Inventors: Aurelien Daynes, Montpellier (FR); Gilles Cauet, Fontanès (FR); Jean-Philippe Gineys, Roquedur (FR); Philippe Nerin, Assas (FR); Jerome Bibette, Paris (FR)

(73) Assignees: HORIBA ABX SAS, Montpellier (FR); Jerome Bibette, Paris (FR)

( * ) Notice: Subject to any disclaimer, the term of this patent is extended or adjusted under 35 U.S.C. 154(b) by 446 days.

(21) Appl. No.: 14/775,886

(22) PCT Filed: Mar. 11, 2014

(86) PCT No.: PCT/FR2014/050544
§ 371 (c)(1),
(2) Date: Dec. 2, 2015

(87) PCT Pub. No.: WO2014/140468
PCT Pub. Date: Sep. 18, 2014

(65) Prior Publication Data
US 2016/0153972 A1    Jun. 2, 2016

(30) Foreign Application Priority Data

Mar. 14, 2013 (FR) .................................... 13 52298

(51) Int. Cl.
*G01N 33/537* (2006.01)
*G01N 33/558* (2006.01)
(Continued)

(52) U.S. Cl.
CPC ..... *G01N 33/537* (2013.01); *G01N 33/54326* (2013.01); *G01N 33/558* (2013.01);
(Continued)

(58) Field of Classification Search
CPC ........... G01N 33/537; G01N 33/54326; G01N 33/558; G01N 33/56966; G01N 2333/4737; G01N 2446/00
See application file for complete search history.

(56) References Cited

U.S. PATENT DOCUMENTS

| 4,879,211 A | 11/1989 | Wang et al. | |
|---|---|---|---|
| 2010/0035243 A1* | 2/2010 | Muller .................. | B82Y 15/00 435/6.11 |

FOREIGN PATENT DOCUMENTS

| CA | 1178886 A | 7/1982 |
|---|---|---|
| EP | 0056018 A2 | 7/1982 |

(Continued)

OTHER PUBLICATIONS

Baudry et al. Acceleration of the recognition rate between grafted ligands and receptors with magnetic forces. PNAS 103 (44): 16076-16078 (Oct. 31, 2006).*

(Continued)

*Primary Examiner* — Gailene Gabel
(74) *Attorney, Agent, or Firm* — Arent Fox LLP

(57) ABSTRACT

The present invention relates to a flow assay method in a liquid medium for an object (or element) of interest via the formation of aggregates of particles that are surface-functionalized by at least one functionalizing molecule, or receptor, specific for said object of interest.

19 Claims, 5 Drawing Sheets

(51) Int. Cl.
    *G01N 33/543*    (2006.01)
    *G01N 33/569*    (2006.01)
(52) U.S. Cl.
    CPC ............ *G01N 33/56966* (2013.01); *G01N 2333/4737* (2013.01); *G01N 2446/00* (2013.01)

(56) References Cited

FOREIGN PATENT DOCUMENTS

EP          2 158 940 A2    3/2010
WO          WO 00/29617 A3  5/2000

OTHER PUBLICATIONS

Gao, "Amperometric Immunisensor Based on Magnetic Inorganic Bionanoparticles Sensing Films", Chinese Journal of Analytical Chemistry, 36(12), 1614-1618, 2008.

Internation Search Report of PCT/FR2014/050544 dated Jul. 14, 2014.

* cited by examiner

FLOW ASSAY METHOD FOR AN OBJECT OF INTEREST

The present invention relates to a method for the flow assaying, in a liquid medium, of an object (or element) of interest via the formation of aggregates of particles which are surface-functionalized with at least one functionalizing molecule, moreover referred to in the text as receptor, specific for said object of interest.

According to the invention, the term "object of interest" is intended to mean any substance with the proviso that it can be specifically recognized by at least two receptors. As object of interest, mention may be made, by way of example and without limitation, of any antigen that can react with an antibody or an aptamer, any nucleic acid molecule that can be recognized by a complementary nucleic acid molecule, any cell or cell fragment or any microorganism or microorganism fragment or else any chemical molecule, as long as they have a known specific receptor. Thus, it appears to be possible to use the method according to the invention for quantifying proteins, antibodies, nucleic acids, cells, cell fragments, microorganisms (for example bacteria, certain fungi, green algae or else viruses), microorganism fragments, or else chemical molecules.

In most laboratory applications, the assaying of a biochemical compound within a biological fluid calls for a reaction aimed at establishing linkages between a substance being sought and a receptor which is specific for said substance. This receptor may, for example, be an antibody or an aptamer in the context of the detection of a protein, or a nucleic acid sequence in the context of the detection of complementary nucleic acid.

An immunodiagnostic system widely used in the prior art is based on the functionalization of microparticles or nanoparticles with receptors, capable of recognizing and binding to the object of interest sought, allowing, in the presence of said object of interest sought, the formation of particulate complexes made up of at least one functionalized particle bound to said object of interest sought by said receptor or a particulate aggregate comprising at least two functionalized particles, bound to one another by an object of interest.

Subsequently, the detection of the particulate complexes or aggregates formed is often carried out by means of an optical measurement. The sensitivity is, for its part, very often linked to the principle of detection used and to the associated instrumentation.

For example, when the object of interest sought is an antigen present in a given medium, said antigen can have several epitopes. Antibodies directed against said antigen can then be chemically attached to the surface of the particles used, in order to functionalize them. When said functionalized particles are introduced into the medium, a reaction can take place between said functionalized particles and said antigen. Thus, a first functionalized particle can capture the antigen sought and form a first particulate complex. However, of course, because of Brownian motion, this same antigen attached to a first functionalized particle can capture a second particle, which is itself functionalized. The two functionalized particles are thus bound by the formation of antibody-antigen-antibody bonds and thus constitute an aggregate. The reaction can continue so as to thus form larger aggregates combining a large number of particles bound to one another according to the same principle.

The presence of aggregates within said medium increases the light scattering, such that the intensity of a light beam passing through said medium is decreased. This is the principle of the optical turbidimetry, the main advantage of which is that it is simple to use, making it possible to envision the manufacture of devices at competitive prices.

However, the performance levels of such a system are relatively limited. Indeed, in order to allow the formation of linkages within a reasonable period of time, the concentration of particles must be considerable. Furthermore, the particles which do not react (particles introduced which have remained free) do not contribute to the useful signal. On the other hand, by virtue of their capacity to scatter light, they contribute to the formation of background noise which can prove to be bothersome for the measurement.

In order to reduce the amount of particles introduced that have remained free, techniques have been developed for increasing the frequency of the collisions between particles. These methods can use magnetic fields [Baudry J. et al., PNAS, 103 (2006) 16076-16078] or electric fields [Iwata K. et al., Annals of Chemical Biochemistry, 46 (2009) 117-122], or ultrasound [Wiklund M., Hertz H. M., Lab on a Chip, 6 (2006), 1279-1292] to locally increase the concentration of particles and to promote the formation of particulate aggregates.

However, even in this case, other problems can be encountered. For example, a concentration of object of interest of less than one picomolar (pM) cannot generally be detected, owing in particular to the thermal fluctuations of the medium which cause fluctuations in the optical signal.

The detection and the assaying of objects of interest, particularly biological objects of interest, in a sample, advantageously a biological sample, by flow measurements are known to those skilled in the art. All the prior art methods use microparticles of which the dispersion level is sufficiently low to allow them to be identified in a two-parameter representation space. For example, the forward scattering (FSC)×side scattering (SSC) two-parameter representation makes it possible to identify the presence of any kind of colloidal aggregates, and processing of the two-parameter representations makes it possible to know the number and the nature of these aggregates. However, when aggregates of more than two particles are formed, even the use of monodispersed particles does not prevent the aggregate populations from overlapping one another.

Generally, the concentration of object of interest is therefore determined by calculating the ratio of the number of aggregates formed to the number of isolated particles, without taking into account the multiplicity of the aggregates. At high concentrations of object of interest, the aggregates may consist of numerous particles. Unfortunately, whatever the size of the aggregates, in the prior art quantification methods, these aggregates, although taken into account, are not weighted by the number of linkages formed. They will then be considered to have the same size as a doublet defined as an aggregate formed by two particles bound to one another by an object of interest, although they represent a larger state of aggregation. Thus, a not insignificant number of linkages created by the object of interest will be neglected, and the accuracy of the measurement will consequently be damaged at high concentrations of objects of interest.

Furthermore, in the prior art, for flow detection, the particles must have a level of quality sufficient to allow their detection for the accurate assaying of the object of interest sought. Ideally, the particles should be identical, in particular in terms of their volume, since two particles taken randomly in the reaction medium should lead to the formation of an aggregate of which the effective cross section must be substantially invariable. Generally, the particles used may be spheres of which the diameters may be randomly distributed about a mean value with a certain standard deviation characteristic of the quality of the fractionation of the particles. It is then considered that the coefficient of variation of the particle size may be less than or equal to 10%. Thus, in the prior art, the implementation of a biological test using flow measurements requires particles of sufficient qualities, the size dispersion of which must be sufficiently controlled and reproducible.

This constitutes a strong industrial constraint since coefficients of variation of less than 10% require considerable manufacturing care resulting in higher cost prices for the particles and, consequently, for the measurement. Furthermore, good control of the coefficient of variation of the particle size is difficult to achieve, in particular when it is sought to give the particles physical properties combining in particular specific physical properties such as fluorescence or magnetism.

As it happens, such properties may be desirable for accelerating the aggregation reaction.

Other techniques for detecting the objects of interest using flow detection of particles exist. Mention may be made of the Luminex technology which detects antigens by virtue of intrinsically fluorescent micrometric particles (primary fluorescence) covered with antibodies specific for said antigen. Once said antigen has been captured by said specific antibodies covering the particles, it is secondarily labeled with a second antibody, which is itself fluorescent (secondary fluorescence) at a wavelength different than that of the primary fluorescence of said particles. The secondary fluorescence is used for the detection of the secondary antibody-antigen complexes. However, it is easily understood that this method requires several steps of, firstly, incubation and then, secondly, of washing in order to remove the excess reagents which might interfere with the measurement. It is therefore longer and more complex to carry out than an aggregation test which requires only one step.

After numerous research studies, the inventors have developed a method for quantifying a given object of interest, based on the determination of the state of aggregation of a suspension of functionalized particles brought into contact with a given object of interest, while overcoming the prior art problems. In particular, the method according to the invention may be applied to sets of functionalized particles which have a considerable size dispersion, which is not the case with the prior art techniques.

The invention therefore aims to provide a novel method for quantifying a presampled given object of interest by flow measurement of the aggregates formed during an object of interest sought/functionalized particle reaction, by means of a method which overcomes all or some of the drawbacks of the known methods of the prior art.

According to the invention, the term "aggregate" is intended to mean a particulate aggregate comprising at least two functionalized particles, bound to one another by an object of interest (doublet). It is therefore understood that, according to the invention, the term "aggregate" is given to any particulate aggregate whether it is made up of two functionalized particles bound to one another by an object of interest or of more than two functionalized particles bound to one another by several objects of interest. It is also understood that the functionalized particles bound to a single object of interest are considered to be singlets.

In the present text, the term "singlet" is therefore intended to mean both the functionalized particles free of any linkage and the objects of interest bound to a single functionalized particle.

The method according to the invention can therefore be likened to an aggregation test (or else agglutination test).

The useful signal in an aggregation test is the number of linkages created between the particles. This measurement can be obtained for a given volume by the difference between the number of singlets present at the beginning of the method (N1) and measured in a given volume (V), and the number (N2) of aggregates and of singlets still present at the end of the aggregation reaction, measured in the same volume (V) at the end of the method. This difference (N1−N2) corresponds to the number of biological linkages formed between 2 functionalized particles during the measurement. In the case where N1 comprises any nonspecific aggregates (aggregates consisting of at least 2 functionalized particles bound to one another by any means other than an object of interest), the measurement by difference according to the invention makes it possible to dispense with said nonspecific aggregates.

According to the invention, the useful signal is the degree of aggregation (DA) which corresponds to the number of biological linkages formed (N1−N2), relative to the total number of singlets (N1), present at the beginning of measurement in the liquid medium comprising said object of interest to be assayed, in other words after introduction and before aggregation. Thus, according to the invention, the degree of aggregation is expressed by $DA=(N1-N2)/N1$.

Thus, the measurements are standardized relative to the initial state of the system, which may contribute to reducing the effect of any errors of preparation of the reaction mixture.

According to the invention, the concentration of object of interest of an unknown sample may be determined with respect to the degree of aggregation measured on a calibration curve pre-established by measuring the degree of aggregation of said functionalized particles in the presence of known amounts of the object of interest.

It is understood from the aforementioned that the novel quantification method according to the invention requires the determination, on the one hand, of the number of singlets present in the reaction medium at the beginning of reaction (N1) and, on the other hand, of the total number of aggregates formed in the reaction medium and of singlets still present at the end of the aggregation reaction (N2).

The numbers (N1) or (N2) can be measured in the following way: each particle or aggregate can be subjected to detection by an optical, electrical or other method. Thus, the passing of each particle or aggregate across the detector gives rise to a pulse which can be recorded. The total number of pulses during the counting time can then be determined. Before the aggregation step, a number N1 of singlets is measured. After the aggregation step, a number N2 of aggregates and of remaining singlets is measured. According to the invention, each aggregate formed, whatever its size, comprising k particles agglutinated by k−1 linkages, is counted as a single element.

In addition, the method according to the invention makes it possible to dispense with a separation of the populations on a single-parameter or multi-parameter representation.

The method according to the invention makes it possible to measure the number of linkages while avoiding relying on the variation of one or more physical parameters of the objects detected; the advantage of not relying on the variation of a physical parameter is that a small aggregate might have a size smaller than a large particle, leading to incorrect classification of the objects studied.

The method according to the invention makes it possible to take into account all the aggregates as previously defined, in such a way that, even at high concentrations of objects of interest, each aggregate formed will be considered individually. Thus, all the linkages created by the objects of interest will be taken into account and the accuracy of the measurement is improved thereby, particularly in the case of a high concentration of objects of interest Another advantage of the method according to the invention lies in the fact that a greater choice of particles is available for carrying out the reaction. In particular, particles which have advantageous properties, such as the superparamagnetic nature, may be used to promote the reaction, whereas the existing detection techniques prevent their use, because of their size dispersion.

Thus, a first subject of the invention is a method for quantifying, in a liquid medium, at least one object of interest, characterized in that it uses particles that are surface-functionalized with at least one receptor specific for said object of interest to be assayed and in which, in:

a first step, said functionalized particles are brought into contact with the object of interest to be assayed, mixing is carried out for a given time ($t_1$) and a volume (v) of said mixture obtained is immediately sampled, and the number N1 of nonaggregated particles (singlets) is counted therein by means of a flow measurement;

a second step, said mixture obtained in step 1 is incubated for a time ($t_2$) sufficient to allow the formation of aggregates and a volume (v) is sampled and the number N2 corresponding to both the nonaggregated particles and the aggregates contained in the volume (v) after reaction is counted using the same flow measurement technique as that used in step 1;

a third step, the degree of aggregation DA=(N1−N2)/N1 (calculated DA) is determined and said object of interest is quantified by comparison of the calculated DA with a standard range (DA=f([C]) previously produced by measuring the degree of aggregation obtained using the same flow measurement technique with the same object of interest at predetermined concentrations ([C]) of said object of interest.

By way of example, the object of interest to be assayed can be contained in a medium such as biological fluids, among which are body fluids, for instance blood, serum, plasma, saliva, urine or cerebrospinal fluid, or else tissue extracts such as bone marrow. Mention may also be made, for example, of purification plant waste, water intended for consumption, etc. Advantageously, the invention is aimed at biological fluids or tissue extracts.

The collisions between the functionalized particles are due to natural Brownian motion. Said motion depends on several parameters which naturally influence the frequency of the collisions. It is possible to adjust these parameters in order to create favorable conditions for having a sufficient period of time, before the first collisions take place, during which it is possible to analyze the medium before said aggregation reaction occurs, so as, for example, to measure the amount of singlets present at the beginning of reaction (N1).

Moreover, techniques for increasing the frequency of the collisions between particles and thus considerably accelerating the aggregation reaction are known. The method according to the invention may or may not include such a step of acceleration of the aggregation reaction by application during the method of a known technique for increasing the frequency of the collisions between particles.

Thus, according to the invention, the quantification method may also comprise a step for increasing the frequency of the collisions between particles, it being possible for said step to be between the end of the first step and the beginning of the second or else to be integrated into the second step.

According to the invention, the term "functionalized particles" is intended to mean any type of functionalized particles described in the prior art and that can be used according to the invention. By way of example, mention may be made of metal beads or plastic beads, for instance polystyrene beads or silica or polymer particles or else particles of the mixed compositions (mixed particles), for instance plastic-covered iron oxide particles, or else non-solid particles, for instance liposomes. Preferentially according to the invention, mixed particles may be used.

According to the invention, the size of said particles may be between 5 and 10 000 nm, and more preferentially between 100 and 1000 nm.

According to one form of the invention, said particles may be sensitive or may have been made sensitive to the techniques that can be used for increasing the frequency of the collisions between particles, such as techniques using magnetic or electric fields or ultrasound. Preferentially, magnetic particles will be used according to the invention.

By way of magnetic particles, use may be made according to the invention of paramagnetic, diamagnetic, ferromagnetic or ferrimagnetic or else superparamagnetic particles. The use of such particles makes it possible to accelerate the aggregation step and to generate a greater signal. When they are subject to a magnetic field, these particles become organized in chains. The local concentration is increased, and the reaction is accelerated.

Thus, aggregates can be formed with low concentrations of objects of interest and of particles. The number of biological linkages formed is then low, owing to the low concentration of the various species. The flow measurement methods are particularly suitable for measuring small amounts of particles, and can therefore be advantageously used in the quantification method according to the invention for measuring the degree of aggregation of magnetic particles.

Those skilled in the art will without difficulty be able to choose the particles suitable for the measurement that they wish to carry out from the numerous known suppliers. Advantageously according to the invention, it is possible to use superparamagnetic particles such that, in an appropriate magnetic field, they retain a capacity to revolve on themselves under the effect of Brownian motion while forming chains.

Consequently, any known flow measurement methods can be used according to the invention, for instance flow cytometry or else capillary electrophoresis or flow in a microfluidic channel. Advantageously according to the invention, flow cytometry may be used.

According to the invention, said specific receptor may be natural or synthetic, for instance a peptide, a protein, a nucleic acid, a saccharide, a lipid, a hormone, and any other biological or synthetic substance as long as said receptor is capable of binding with the object of interest (Antibodies a laboratory manual E. Harlow and D. Lane, Cold Spring Harbor Laboratory, 1988).

Those skilled in the art will without difficulty be able to graft, if necessary, receptors onto particles.

These receptors may be immobilized at the surface of the particles by various techniques known to those skilled in the art, for example by adsorption, covalent and/or high-affinity interactions. For information, reference may be made to the handbook "Bioconjugate Techniques" by G. T. Hermanson (Academic Press, 1996).

The method according to the invention uses reaction conditions known to those skilled in the art that they will thus have no difficulty in implementing.

According to the invention, it is possible to add to the reaction mixture of the first step a nonionic (Tween® 80), ionic (sodium cholate, sodium taurocholate) or else zwitterionic (3-[(3-cholamidopropyl)dimethylammonio]-1-propanesulfonate (CHAPS)) detergent, a solution of proteins (bovine serum albumin (BSA)), or polymers (polyvinyl alcohol (PVA)).

The addition of a detergent makes it possible to prevent two particles from remaining bound after a collision without however an object of interest being involved. Nonspecific aggregations are thus prevented.

According to the invention, the duration of the first step is short and lasts approximately only the time t1 of rapid mixing of the particles in the medium. Thus, the first step may last from a few seconds to a few minutes, advantageously at most 3 minutes, very advantageously 2 minutes.

This first step of the method, according to the invention, makes it possible to measure the number N1 of nonaggregated functionalized particles in the volume (v) sampled at the beginning of the reaction. For this, a fraction of the reaction mixture can be sampled as soon as the particles are introduced into the sampled volume (v) containing the object of interest to be assayed and analyzed. Since the time elapsed between the introduction of the particles and the sampling of an aliquot of said mixture is short compared with the time for passive aggregation of the particles in the liquid medium, this value N1 corresponds to the concentration of nonaggregated functionalized particles introduced into said liquid medium at the beginning of the reaction.

According to the invention, the duration of the second step may be between 5 seconds and 3 hours, preferentially between 5 and 60 minutes. This time may allow the formation of the maximum amount of aggregates of all sizes, but must remain compatible with a reasonable total duration of the measurement.

According to one variant of the invention, just before the second step of the method or during the second step, a magnetic field, an electric field or ultrasound may be applied in order to increase the frequency of the collisions between particles.

For example, if a magnetic field is applied, the medium may undergo from 1 to 10 field cycles of 3 mT to 100 mT, it being possible for each cycle to have a duration of 1 to 600 seconds, preferentially of 100 to 500 seconds, advantageously 300 seconds alternating with periods of relaxation (no field applied).

According to the invention, in the third step of the method, the degree of aggregation DA=(N1−N2)/N1 is calculated (calculated DA). The concentration of object of interest in the sample can then be determined by comparison of the calculated DA with a standard range of DA pre-established by measuring the aggregation of the particles in the presence of known amounts of the same object of interest.

FIG. 1 is a diagrammatic representation of the principle of the method according to the invention with, on the left part of the diagram, a representation of the functionalized particles free of any linkage and the objects of interest bound to a single functionalized particle (singlets). It is the number N1 of singlets which is measured in the first step of the method according to the invention. On the right part of the diagram are represented, on the one hand, the singlets still present after aggregation (nα), or the functionalized particles involved in aggregates (nβ), the sum nα+nβ corresponding to the number N2 of singlets and of aggregates after aggregation. It is thus understood that N1−N2 (10−6=4) corresponds to the number of linkages in the nβ (3) aggregates formed and that, in this theoretical case, the degree of aggregation (DA) is equal to (N1−N2)/N1=(10−6)/10=0.4.

FIG. 2 shows the results of the detection by the automated device for an aggregation in presence of 1 pM of CRP. The continuous-line curve represents the pulses detected for 30 seconds by the automated measuring device before aggregation. The sum of these pulses corresponds to N1. The dashed-line curve represents the pulses detected for 30 seconds by the automated measuring device after aggregation. The sum of these pulsed corresponds to N2.

FIG. 4 shows the standard curve obtained by measuring the degree of aggregation of particles of 200 nm for various concentrations of biotinylated bovine serum albumin (0 to 500 pM).

Figure 1:
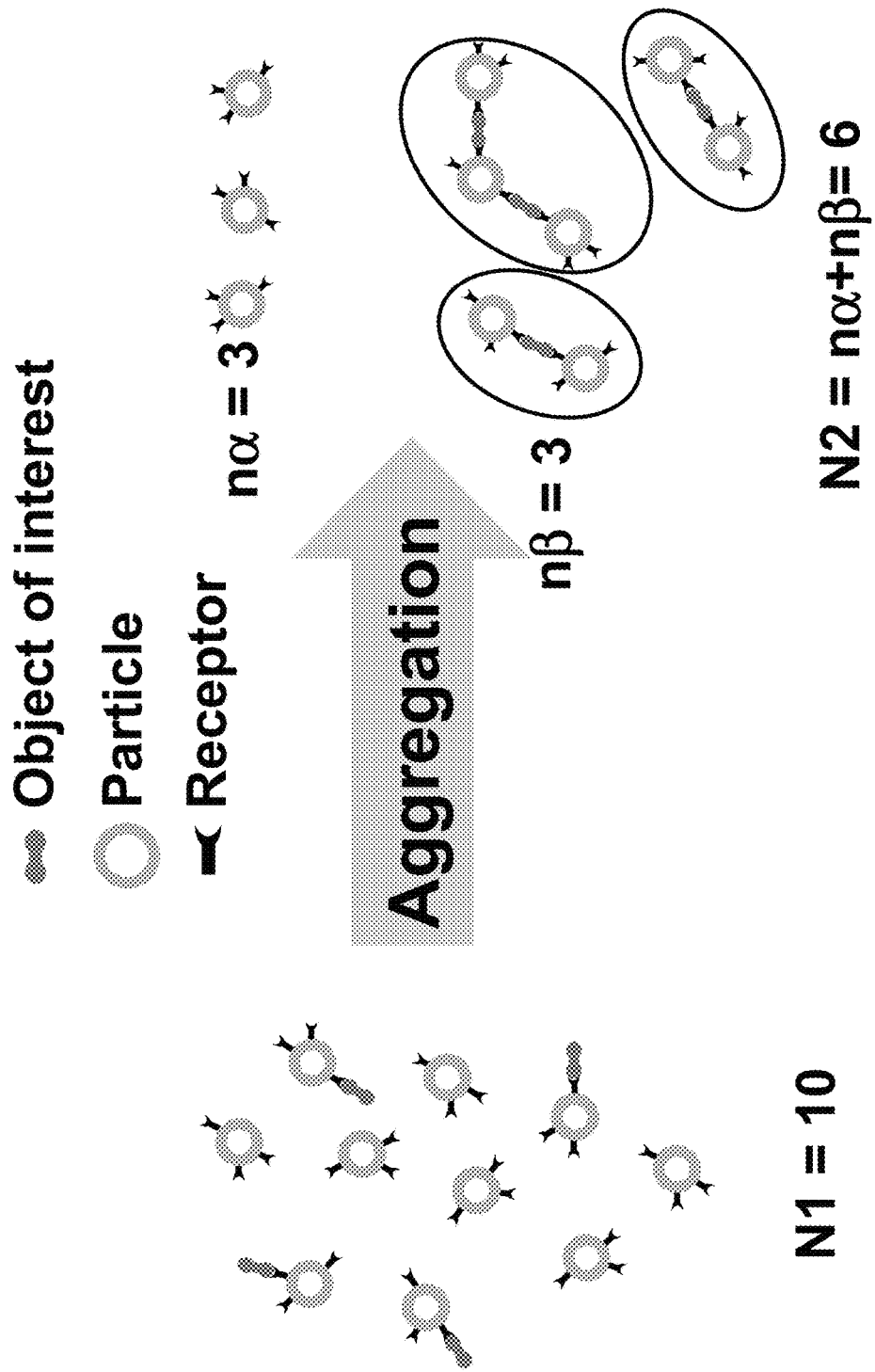

Other subjects, characteristics and advantages of the invention may emerge from the examples which follow.

EXAMPLE 1: ASSAYING OF CRP (C-REACTIVE PROTEIN) USING SUPER-PARAMAGNETIC PARTICLES 500 nm IN DIAMETER

Anti-CRP polyclonal antibodies (L66616G, Meridian Life Science) (approximately 10 μg of antibodies per mg of beads) were grafted onto superparamagnetic particles 500 nm in diameter (MasterBeads Carboxylic Acid 0215, Ademtech).

The assays were carried out in a 30 mM glycine buffer, pH 8.5, containing variable concentrations of CRP (ABX Pentra CRP cal, Horiba Medical).

In order to limit the formation of linkages between particles in the absence of CRP, taurocholic acid (T4009, Sigma-Aldrich) was added to the medium at a final concentration of 3 mM in the reaction mixture.

The final concentration of particles in the medium is approximately 0.6 pM. The flow analysis is carried out by illuminating the particles with a laser working at 488 nm. The scattering at 90° is measured for each object passing through the measuring cell using a photomultiplier of the Hamamatsu brand, model H9307-02.

After the various reagents have been brought into contact, the medium is left to incubate for 2 min. During these 2 min, a volume (V1) of 53 μl of the mixture is sampled and injected into the flow analyzer. The latter dilutes the volume V1 to 1/100 and performs a count for 30 s on a volume V2 of 35.5 μl of this mixture. The number of singlets present in the suspension at the beginning of the reaction (N1) in said volume V2 is then determined.

After 2 min, the medium undergoes 5 field cycles, composed of 30 s under 10 mT, then 300 s under 3 mT and, finally, 30 s of relaxation under 0 mT.

After the magnetization cycle, a second volume (V1) of the mixture, identical to the volume previously sampled (53 μl), is sampled and analyzed by the flow analyzer according to the same preparation cycle. This measurement makes it possible to determine the number of aggregates formed (N2).

Figure 2:
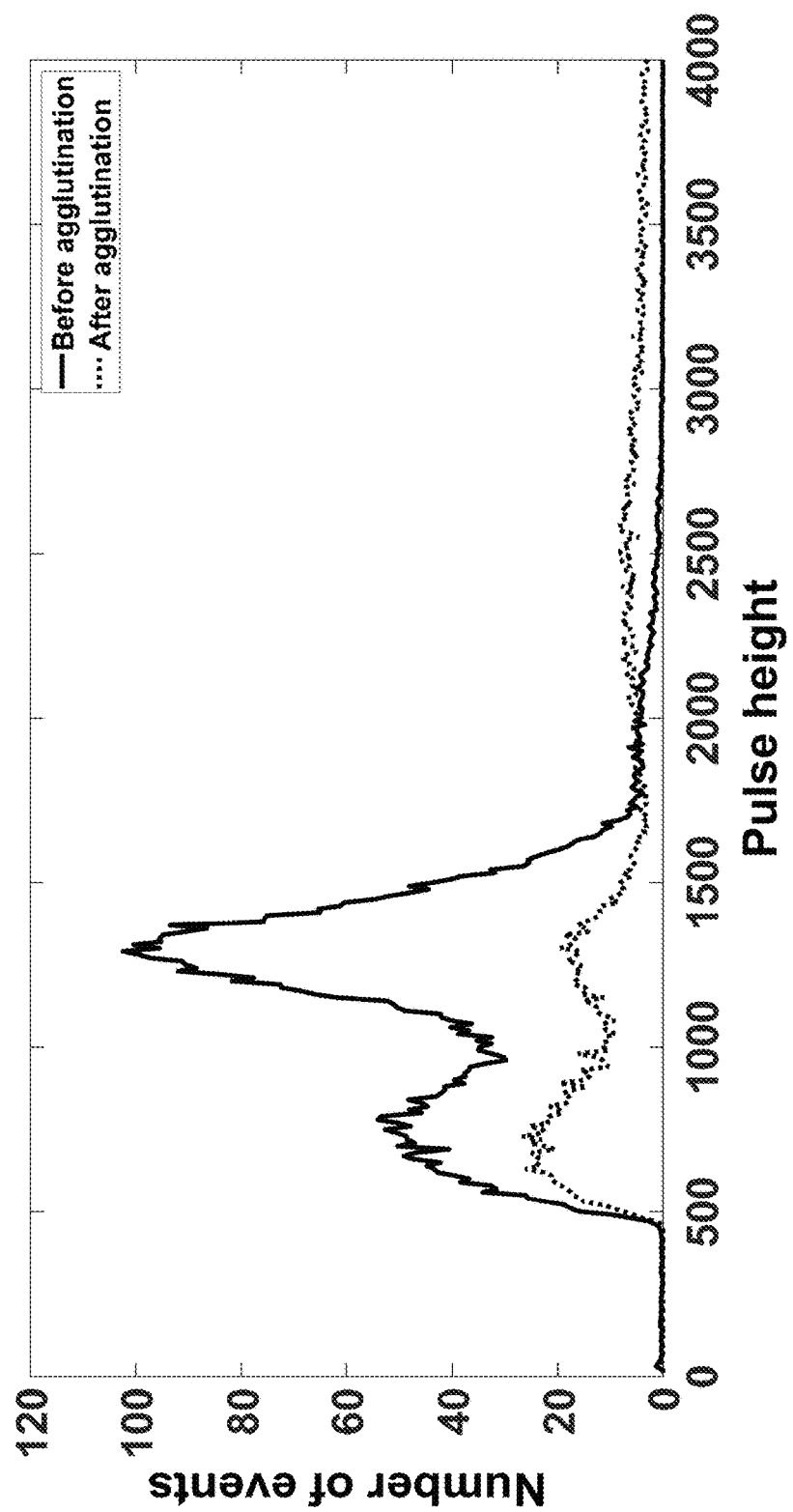

FIG. 2 shows the results of the detection by the automated device for an aggregation in the presence of 1 pM of CRP. It represents the number of elements detected in the volume (V2) for 30 seconds as a function of the height of the pulse which is associated with said elements, itself a function of the size of the object. It is noted that, before aggregation (continuous line), the suspension has a complex distribution with numerous sizes of particles present. After aggregation (dashed line), no population clearly associated with the particle aggregates is apparent; however, the total number of objects detected (area under the curve) has clearly decreased.

Figure 3:
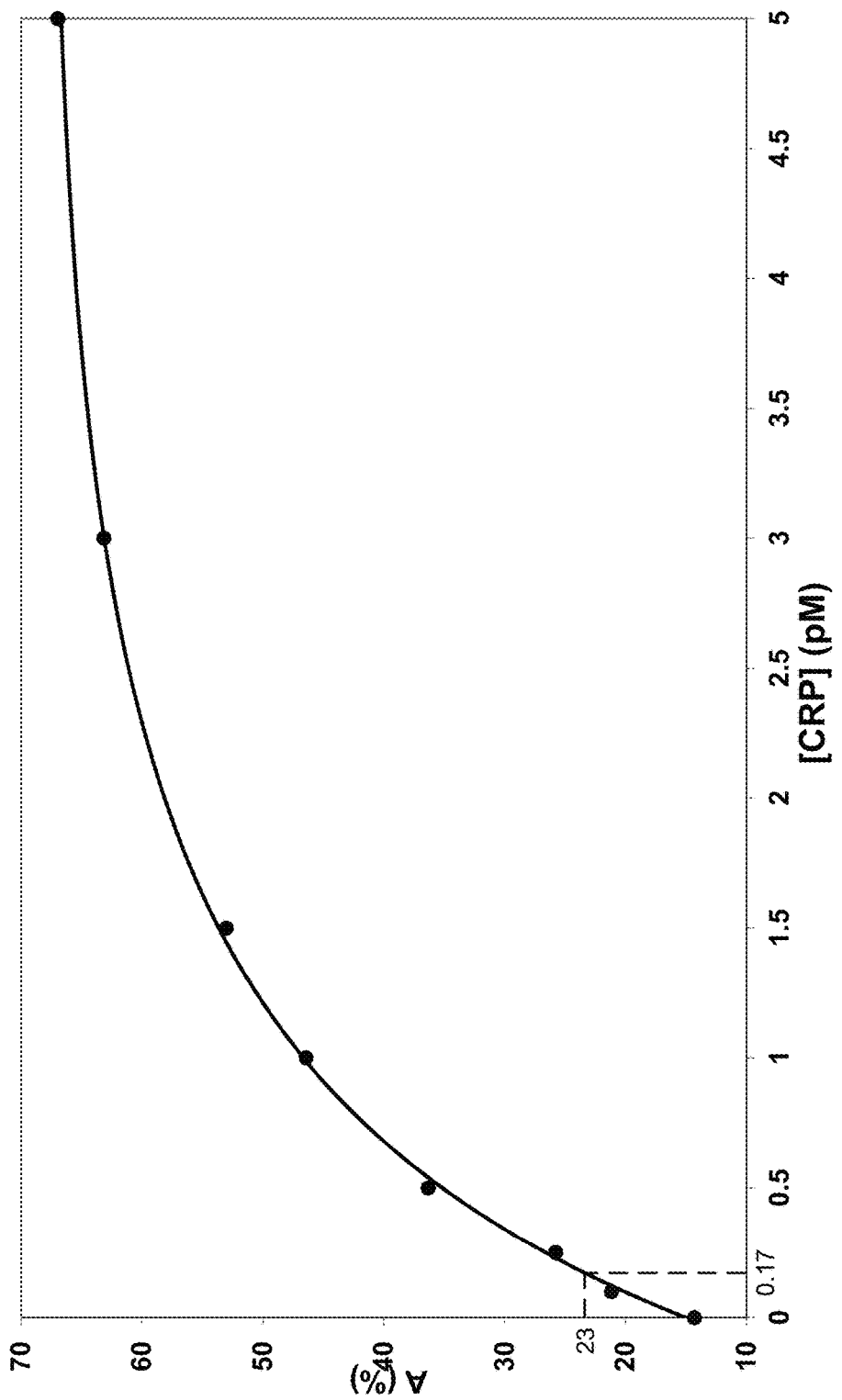
FIG. 3 shows the standard curve obtained by measuring the degree of aggregation of particles of 500 nm for various CRP concentrations (0 to 5 pM).

Establishment of the Standard Curve:

The degree of aggregation was determined for various CRP concentrations (from 0 to 5 pM) according to the protocol previously described. The results are presented in FIG. 3.

It is noted that the degree of aggregation actually varies with the CRP concentration in the medium. On the bases of the standard deviation measured on several repetitions in the absence of CRP, the detection limit of this system could be evaluated at 25 fM of CRP, for an analysis time of approximately 35 min.

Assaying of the CRP concentration in an unknown solution: A serum sample, with an unknown CRP concentration, was diluted 10 000-fold in a 30 mM glycine buffer, pH 8.5. 27.6 µl of this mixture were added to a 30 mM glycine buffer containing the same functionalized superparamagnetic particles 500 nm in diameter (MasterBeads Carboxylic Acid 0215, Ademtech) as previously used, and also taurocholic acid. The final volume of the medium is 600 µl, with a final concentration of particles of 0.6 pM and of taurocholic acid of 3 mM.

After the various reagents have been brought into contact, the Medium is left to incubate for 2 min. During these 2 min, a volume (V1) of 53 µl of the mixture is sampled and injected into the flow analyzer. The latter dilutes the volume V1 to 1/100 and performs a count for 30 s on a volume (V2) of 35.5 µl of this mixture. The number of singlets present in the suspension at the beginning of the reaction (N1) in said volume V2 is then determined.

After 2 minutes, the medium undergoes 5 field cycles, composed of 30 s under 10 mT, 30 s under 3 mT and 30 s of relaxation under 0 mT.

After the magnetization cycle, a second volume (V1) of the mixture, identical to the volume previously sampled (53 µl), is sampled and analyzed in a manner identical to the first sampling in order to determine the value of N2.

According to the protocol previously described, it was thus possible to determine, for the unknown sample, a degree of agglutination DA=0.23. Relating this to the calibration curve makes it possible to determine a CRP concentration in the reaction medium equal to 0.17 pM, i.e. a CRP concentration in the unknown serum of 37 nM.

EXAMPLE 2: ASSAYING OF CRP USING SUPERPARAMAGNETIC PARTICLES OF 200 nm

Establishment of the Standard Curve:

Approximately 35 µg of anti-CRP polyclonal antibodies (L66616G, Meridian Life Science) per mg of particles were grafted onto magnetic particles 200 nm in diameter (Carboxyl Adembeads, 0212, Ademtech).

The assays were carried out in a 30 mM glycine buffer, pH 8.5, containing variable concentrations of CRP (ABX Pentra CRP cal, Horiba Medical).

In order to limit the formation of linkages between particles in the absence of CRP, saponin (30502-42, Nacalai Tesque) was added to the medium at 0.08% by weight in the reaction mixture as detergent.

The final concentration of particles in the medium is approximately 3 pM.

After the various reagents have been brought into contact, the medium is left to incubate for 2 min. During these 2 minutes, a volume (V1) of 53 µl of the mixture is sampled and injected into the flow analyzer. The latter dilutes the volume V1 to 1/1200 and performs a count for 30 s on a volume (V2) of 35.5 µl of this mixture. The number of singlets present in the suspension at the beginning of the reaction (N1) in said volume V2 is then determined.

After 2 minutes, the medium undergoes 2 magnetic field cycles, composed of 30 s under 50 mT, 300 s under 20 mT and 30 s of relaxation under 0 mT.

After the magnetization cycle, a second volume (V1) of the mixture, identical to the volume previously sampled (53 µl), is sampled and analyzed in a manner identical to the first sampling in order to determine the value of N2. This measurement makes it possible to determine the number of aggregates formed (N2).

Figure 4:
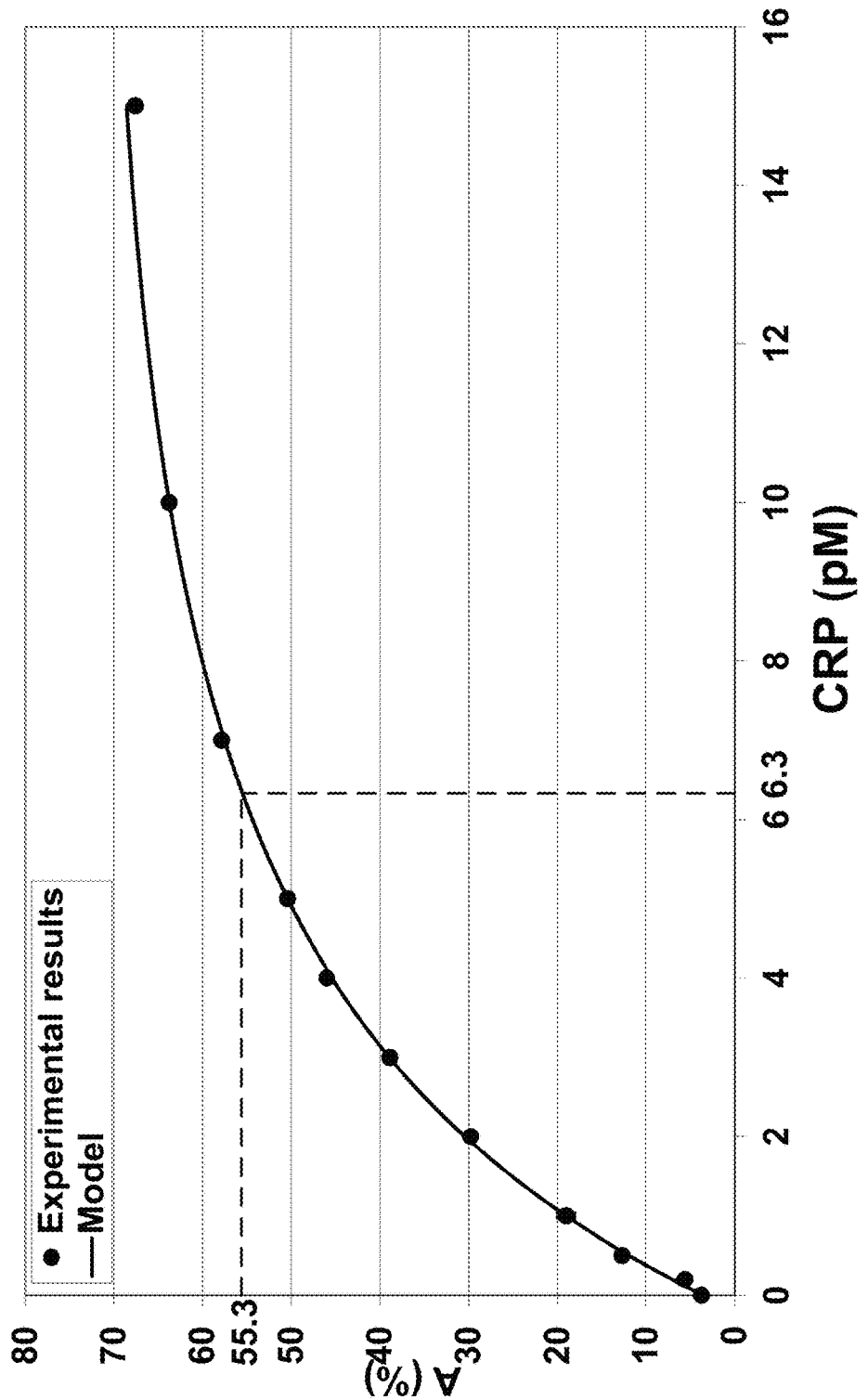
FIG. 4 shows the standard curve obtained by measuring the degree of aggregation of particles of 200 nm for various CRP concentrations (0 to 15 pM).

The degree of aggregation was determined for various CRP concentrations (from 0 to 16 pM) according to the protocol previously described. The standard curve obtained is given in FIG. 4.

On the basis of the repetitions in the absence of CRP, the detection limit was evaluated at 100 fM of CRP, for an analysis time of approximately 15 min.

Assaying of the CRP Concentration in an Unknown Solution:

A serum sample, with an unknown CRP concentration, was diluted 100-fold in a 30 mM glycine buffer, pH 8.5. 2 µl of this mixture were added to a 30 mM glycine buffer containing the same functionalized magnetic particles 200 nm in diameter, and also saponin. The final volume of the medium is 600 µl, with a final concentration of particles of 3 pM and of saponin of 0.08% (weight/volume).

After the various reagents have been brought into contact, the medium is left to incubate for 2 min. During these 2 min, a volume (V1) of 53 µl of the mixture is sampled and injected into the flow analyzer. The latter dilutes the volume V1 to 1/1200 and performs a count for 30 s on a volume (V2) of 35.5 µl of this mixture. The number of singlets present in the suspension at the beginning of the reaction (N1) in said volume V2 is then determined.

After 2 min, the medium undergoes 2 field cycles, composed of 30 s under 50 mT, 300 s under 20 mT and 30 s of relaxation under 0 mT.

After the magnetization cycle, a second volume (V1) of the mixture, identical to the volume previously sampled (53 µl), is sampled and analyzed in a manner identical to the first sampling in order to determine the value of N2. This measurement makes it possible to determine the number of aggregates formed (N2).

It was thus possible to determine, for the unknown sample, a degree of agglutination DA=0.55. Relating this to the calibration curve makes it possible to determine a CRP concentration in the reaction medium equal to 6.3 pM, i.e. a CRP concentration in the unknown serum of 189 nM.

EXAMPLE 3: ASSAYING OF BIOTIN USING SUPERPARAMAGNETIC PARTICLES of 200 nm

Establishment of the Standard Curve:

Streptavidin-covered particles 200 nm in diameter were used (Bio-Adembeads Streptavidin 0312, Ademtech).

The assays were carried out in a 30 mM glycine buffer, pH 8.5, containing 0.5% of bovine serum albumin (BSA Protease Free, ID Bio) and also variable concentrations of biotinylated bovine serum albumin (BSAb) (A8549, Sigma-Aldrich). The final concentration of particles in the medium is approximately 6 pM.

After the various reagents have been brought into contact, the medium is left to incubate for 2 min. During these 2 min, a volume (V1) of 53 µl of the mixture is sampled and injected into the flow analyzer. The latter dilutes the volume V1 to 1/2400 and performs a count for 30 s on a volume (V2) of 35.5 µl of this mixture. The number of singlets present in the suspension at the beginning of the reaction (N1) in said volume V2 is then determined.

After 2 min, the medium undergoes 2 field cycles, composed of 30 s under 50 mT, 300 s under 20 mT and 30 s of relaxation under 0 mT.

After the magnetization cycle, a second volume (V) of the mixture, identical to the volume previously sampled (53 µl), is sampled and analyzed in a manner identical to the first sampling in order to determine the value of N2. This measurement makes it possible to determine the number of aggregates formed (N2).

Figure 5:
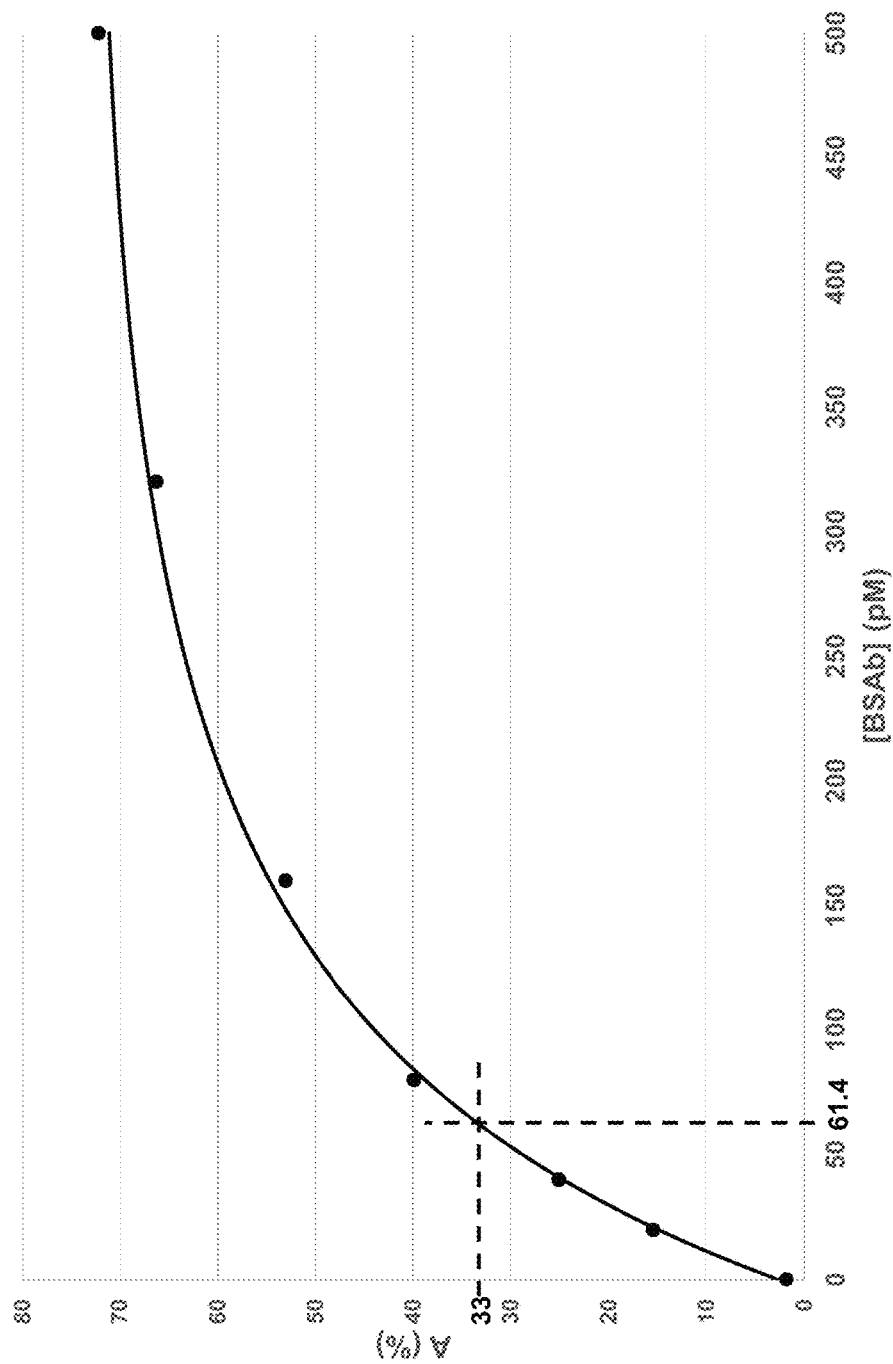

The degree of aggregation was determined for various biotin concentrations (from 0 to 500 pM) according to the protocol previously described. The standard curve obtained is given in FIG. 5. On the basis of the repetitions in the absence of biotinylated BSA, the detection limit was evaluated. The experimental conditions were not optimized for this assay, and a high detection limit, of about 7 pM of biotinylated BSA, is found for an analysis time of approximately 15 min.

Assaying of the Biotin Concentration in an Unknown Solution:

A sample with an unknown BSAb concentration was diluted 10-fold in a 5% BSA solution. 60 µl of this mixture were added to a 30 mM glycine buffer containing the same functionalized magnetic particles 200 nm in diameter, The final volume of the medium is 600 µl, with a final concentration of particles of 6 pM and of BSA of 0.5% (weight/volume).

After the various reagents have been brought into contact, the medium is left to incubate for 2 min. During these 2 min, a volume (V1) of 53 µl of the mixture is sampled and injected into the flow analyzer. The latter dilutes the volume V1 to 1/2400 and performs a count for 30 s on a volume (V2) of 35.5 µL of this mixture. The number of singlets present in the suspension at the beginning of the reaction (N1) in said volume V2 is then determined.

After 2 min, the medium undergoes 2 field cycles, composed of 30 s under 50 mT, 300 s under 20 mT and 30 s of relaxation under 0 mT.

After the magnetization cycle, a second volume (V1) of the mixture, identical to the volume previously sampled (53 µl), is sampled and analyzed in a manner identical to the first sampling in order to determine the value of N2. This measurement makes it possible to determine the number of aggregates formed (N2).

It was thus possible to determine, for the unknown sample, a degree of agglutination DA=0.33. Relating this to the calibration curve makes it possible to determine a BSAb concentration in the reaction medium equal to 61.4 pM, i.e. a BSAb concentration in the unknown sample of 614 pM.

The invention claimed is:

1. A method for quantifying in a liquid medium at least one object of interest, comprising:
   mixing particles surface functionalized with at least one receptor specific for said object of interest to be assayed with the object of interest, for an initial time ($t_1$) to form a first mixture;
   immediately sampling a volume (v) of the first mixture and counting the number N1 of singlets in said volume (v) by flow measurement;
   incubating the first mixture for a second time ($t_2$) sufficient to allow the formation of aggregates, thereby forming a second mixture;
   sampling a volume of the second mixture and counting the number N2 corresponding to both the singlets and the aggregates contained in the volume (v) by the same flow measurement technique as used previously;
   determining a calculated degree of aggregation using the formula DA=(N1−N2)/N1 (calculated DA) and quantifying said object of interest by comparison of the calculated DA with a standard range (DA=f([C]) previously produced by measuring and calculating the degree of aggregation obtained using the same flow measurement technique with the object of interest at predetermined concentrations ([C]) of said object of interest.

2. The method according to claim 1, wherein said object of interest is a protein, an antibody, a nucleic acid, a cell, a cell fragment, a microorganism, a microorganism fragment or a chemical molecule.

3. The method according to claim 1, wherein the object of interest is in a biological fluid, a tissue extract, purification plant waste, or water intended for consumption.

4. The method according to claim 3, wherein said biological fluid is blood, serum, plasma, saliva, urine or cerebrospinal fluid.

5. The method according to claim 3, wherein the object of interest is in a biological fluid or a tissue extract.

6. The method according to claim 3, wherein said tissue extract is bone marrow.

7. The method according to claim 1, wherein said receptor is a peptide, a protein, a nucleic acid, a saccharide, a lipid, or a hormone.

8. The method according to claim 1, wherein the aggregates have a size between 5 and 10,000 nm.

9. The method according to claim 8, wherein the aggregates have a size between 100 and 1000 nm.

10. The method according to claim 1, wherein the functionalized particle is a magnetic particle.

11. The method according to claim 1, wherein the initial time ($t_1$) is less than three minutes.

12. The method according to claim 11, wherein the initial time ($t_1$) is at most 2 minutes.

13. The method according to claim 1, further comprising increasing the aggregate collision frequency during the second time ($t_2$).

14. The method according to claim 13, wherein the frequency of the collisions is increased by a magnetic or electric field or ultrasound.

15. The method according to claim 1, wherein the second time ($t_2$) is between 5 seconds and 3 hours.

16. The method according to claim 15, wherein the second time ($t_2$) is between 5 minutes and 60 minutes.

17. The method according to claim 1, wherein the flow measurement is carried out in flow mode.

18. The method according to claim 17, wherein the measurement is carried out by flow cytometry, capillary electrophoresis, or flow in a microfluidic channel.

19. The method according to claim 18, wherein the measurement is carried out by flow cytometry.

* * * * *